United States Patent [19]

Lew

[11] Patent Number: 5,005,426

[45] Date of Patent: Apr. 9, 1991

[54] MASS-VOLUME VORTEX FLOWMETER

[76] Inventor: Hyok S. Lew, 7890 Oak St., Arvada, Colo. 80005

[21] Appl. No.: 492,943

[22] Filed: Mar. 13, 1990

Related U.S. Application Data

[63] Continuation-in-part of Ser. No. 208,739, Jun. 20, 1988, Continuation-in-part of Ser. No. 368,406, Jun. 19, 1989.

[51] Int. Cl.$^5$ .............................................. G01F 1/32
[52] U.S. Cl. .................................. 73/861.22; 73/195
[58] Field of Search ............... 73/195, 861.02, 861.03, 73/861.22, 861.24

[56] References Cited

U.S. PATENT DOCUMENTS

| | | | |
|---|---|---|---|
| 3,937,195 | 2/1976 | Woods | 73/861.22 X |
| 4,116,060 | 9/1978 | Frederick | 73/861.22 |
| 4,437,349 | 3/1984 | Joy | 73/861.22 |
| 4,630,484 | 12/1986 | Mizuno et al. | 73/861.22 |

*Primary Examiner*—Herbert Goldstein

[57] ABSTRACT

A flowmeter comprises a first combination of vortex generator and sensor and a second combination of vortex generator and sensor wherein the first vortex shedding frequency measured by the first combination of vortex generator and sensor is proportional to the volume flow rate of fluid and the second vortex shedding frequency measured by the second combination of vortex generator and sensor is a function of the dynamic pressure of the fluid flow; wherein the volume flow rate of the fluid is determined from the first vortex shedding frequency, while the mass flow rate is determined from a combination of the first and second vortex shedding frequencies.

6 Claims, 2 Drawing Sheets

MASS-VOLUME VORTEX FLOWMETER

BACKGROUND OF THE INVENTION

This is a continuation-in-part application to patent applications Ser. No. 208,739 entitled "Three-In-One Flowmeter" filed on Jun. 20, 1988 and Ser. No. 368,406 entitled "Mass-Volume Flowmeter" filed on Jun. 19, 1989.

In contrast to flowmeters of the present day technology which measure only one of the two flow rates, i.e., the mass flow rate or the volume flow rate, the flowmeters of future technology will measure the mass and volume flow rates as well as the density of media. The three-in-one flownmeters providing all of the three flow variables will cost slightly more than the present day flowmeters measuring only one of the three flow variables and, consequently, there is little doubt that the future flowmeter market will be dominated by one or other types of three-in-one flowmeters.

BRIEF SUMMARY OF THE INVENTION

The primary object of the present invention is to provide a vortex generating bluff body of variable width that varies as a function of the dynamic pressure of moving fluid.

Another object is to provide a mass-volume vortex flowmeter comprising a first vortex generating bluff body of fixed width and a second vortex generating bluff body of variable width disposed downstream of the first vortex generating bluff body; wherein the volume flow rate is determined from the frequency of vortex shedding from the first vortex generating bluff body, and the mass flow rate is determined from a combination of two frequencies of vortex shedding from the first and second vortex generating bluff bodies.

A further object is to provide a mass-volume vortex flowmeter comprising a first vortex generating bluff body disposed across an upstream cross section of a flow passage having a constant cross section area, and a second vortex generating bluff body disposed across a downstream cross section of the flow passage having a variable cross section area that changes as a function of the dynamic pressure of fluid flow; wherein the volume flow rate is determined from the frequency of vortex shedding from the first vortex shedding bluff body, and the mass flow rate is determined from a combination of two frequencies of vortex sheddings from the first and second vortex shedding bluff bodies.

Yet another object is to provide a mass-volume vortex flowmeter comprising two flow passages disposed in a parallel arrangement; wherein one of the two flow passages includes a vortex generating bluff body of fixed width, and the other of the two flow passages includes a vortex generating bluff body of variable width that varies as a function of the dynamic pressure of moving fluid. The volume flow rate is determined from and additive combination of two frequencies of vortex sheddings from the two vortex shedding bluff bodies, and the mass flow rate is determined from a level of inequality between the two vortex shedding frequencies.

These and other objects of the present invention will become clear as the description thereof progresses.

BRIEF DESCRIPTION OF THE FIGURES

The present invention may be described with a greater clarity and specificity by referring to the following figures.

DESCRIPTION OF THE ILLUSTRATED EMBODIMENTS

Figure 1:
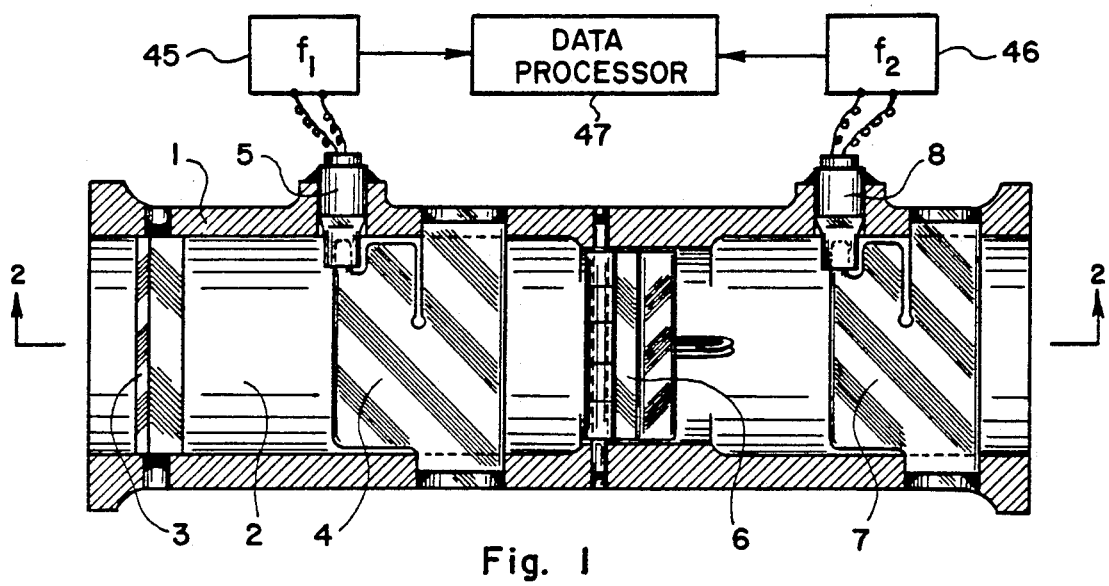
FIG. 1 illustrates a cross section of an embodiment of the mass-volume vortex flowmeter of the present invention including a fixed width vortex generatin bluff body and a variable width vortex generating bluff body.

In FIG. 1 there is illustrated a cross section of an embodiment of the mass-volume vortex shedding flowmeter of the present invention. The flowmeter body 1 includes a flow passage 2 extending therethrough. A first combination of vortex generator-sensor includes a vortex generating bluff body 3 of fixed width and a vortex sensing planar member 4 connected to a transducer 5 that converts the alternating lift force generated by the vortices shed from the bluff body 3 and experienced by the planar member 4 to an alternating electrical signal. A second combination of vortex generator-sensor disposed downstream of the first combination includes a vortex generating bluff body 6 of variable width that changes as a function of the dynamic pressure of the fluid flow and a vortex sensing planar member 7 connected to a transducer 8. The dynamic pressure of fluid flow is equal to one half of the fluid density times square of the fluid velocity. It should be mentioned that the vortex generator-sensor comprising separate vortex generating bluff body and vortex sensing planar member employed in the particular illustrative embodiment may be replaced by a vortex generator-sensor constructed in an integral structure such as that shown in FIG. 4. While it is preferred to install the bluff body of fixed width across an upstream cross section and the bluff body of variable width across a downstream cross section of the flow passage, they may be installed in reversed order.

Figure 2:
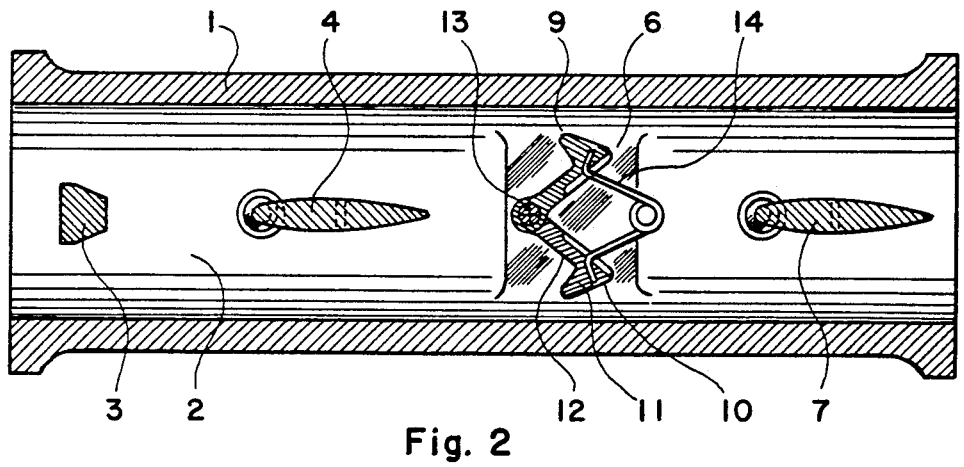
FIG. 2 illustrates another cross section of the embodiment shown in FIG. 1.

In FIG. 2 there is illustrated another cross section of the embodiment shown in FIG. 1, which cross section is taken along plane 2—2 as shown in FIG. 1. In contrast to the vortex generating bluff body 3 of fixed width having a one piece cylindrical shape, the vortex generating bluff body 6 of variable width comprises two symmetric halves 9 and 10, each of which includes a blunt cylindrical portion 11 resembling one side half of the bluff body 3 of fixed width, that is supported by a planar member 12 secured to the flowmeter body 1 in a pivoting relaitonship about an axis 13 perpendicular to the central axis of the flow passage 2. The two halves 9 and 10 of the bluff body 6 includes a spring bias 14 that tends to spread the two halves 9 and 10 of the bluff body 6 and, consequently, increases the width of the bluff body 6. It is a well known fact that the frequency $f_1$ of the vortex shedding from the first bluff body 3 with fixed width $b_1$ is related to the fluid velocity U by equation $$f_1 = \frac{S_t}{b_1} U, \quad (1)$$

where $S_t$ is a dimensionless constant known as Strouhal number. The dynamic pressure of the fluid flow tends to fold the two halves 9 and 10 of the second bluff body 6 against the spring bias force and, consequently, the effective width $b_2$ of the second bluff body 6 is a function of the dynamic pressure of fluid flow and can be expressed by equation $$b_2 = F(\rho U^2/2), \quad (2)$$

where F stands for an empirically determined mathematical relationship. The use of equation (2) yields the following equation equivalent to equation (1):

$$f_2 = \frac{S_t U}{F(\rho U^2/2)}, \quad (3)$$

where $f_2$ is the frequency of vortex shedding from the second bluff body 6 of variable width. It should be mentioned that $S_t$ appearing in equation (3) may or may not have the same numerical value as that appearing in equation (1) depending on the width of the vortex generating bluff body relative to the cross section dimension of the flow passage. By solving equation (3) for the dynamic pressure of fluid flow and substituting equation (1) thereinto, the following equation can be obtained:

$$\frac{1}{2} \rho U^2 = F^{-1}\left(\frac{b_1 f_1}{S_t' f_2}\right), \quad (4)$$

where $F^{-1}$ stands for the inverse relationship of F and $S_t'$ is the ratio of Strouhal numbers. The fluid velocity or volume flow rate is determined from equation (1) as a function of the vortex shedding frequency $f_1$, while the dynamic pressure of the fluid flow is determined from equation (4) as a function of the ratio of vortex shedding frequencies $f_2/f_1$. The mass flow rate is obtained as the ratio of the dynamic pressure to one half of the fluid velocity, and the density of fluid is obtained as the ratio of mass flow rate to the volume flow rate. "A pair of frequency detectors 45 and 46 respectively determine the vortex shedding frequencies from the two vortex generating bluff bodies 3 and 6. The vortex shedding frequencies $f_1$ and $f_2$ so determined are fed to a data processor or computer 47, that determines the velocity of fluid or the volume flow rate from the vortex shedding frequency $f_1$ and the dynamic pressure of fluid flow as a function of the two vortex shedding frequencies $f_1$ and $f_2$, which data processor also determines the mass flow rate of fluid from a combination of the first vortex shedding frequency $f_1$ and a function of the two vortex shedding frequencies $f_1$ and $f_2$, and the density of fluid as a ratio of the mass flow rate to the volume flow rate."

Figure 3:
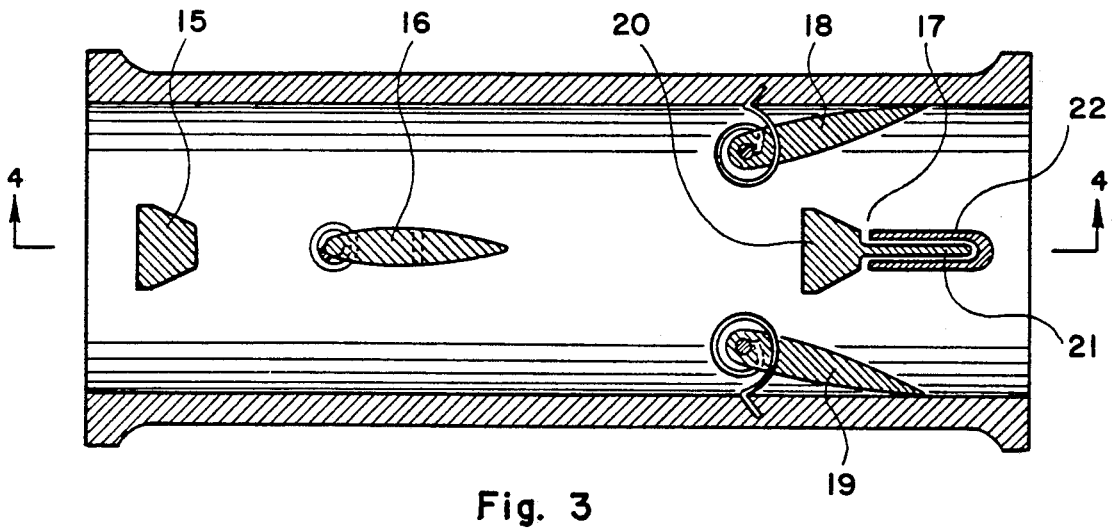
FIG. 3 illustrates a cross section of another embodiment of the mass-volume flowmeter including a first fixed width vortex generating bluff body disposed across a first cross section of a flow passage having a constant cross section area and a second fixed width vortex generating bluff body disposed across a second cross section of the flow passage having a variable cross section area.

In FIG. 3 there is illustrated a cross section of another embodiment of the mass-volume vortex flowmeter, that includes a combination of the vortex generating bluff body 15 of fixed width and the vortex sensing planar member 16, and a vortex generator-sensor disposed across a downstream cross section of the flow passage that has a variable cross section area varying as a function of the dynamic pressure of fluid flow. The variable cross section area of the flow passage is provided by a pair of pivoting gates or flaps 18 and 19 spring biased to keep the gates or flaps 18 and 19 at a closed position. It should be noticed that the first combination of the vortex generator-sensor includes separate vortex generator 15 and vortex sensor 16 having the same construction and operating on the same principles as those described in conjunction with FIG. 1, while the second combination of the vortex generator-sensor 17 has an integral construction wherein the vortex generator and sensor are incorporated into a single integral assembly. The bluff body 20 of fixed width having the same construction as the bluff body 15 has a planar trailing edge extension 21, that is surrounded on three sides by a pressure shield 22 having a U-shaped cross section. The two sides of the combination of the bluff body 20 and planar trailing edge 21 exposed to the fluctuating fluid pressures created by the vortices shed from two sides of the bluff body 20 in an alternating pattern through the openings between the trailing edge of the bluff body 20 and the leading edge of the pressure shield 22 exerts an alternating lift force on the bluff body 20, that is converted to an alternating electrical signal by a transducer connected to one extremity of the bluff body 20.

Figure 4:
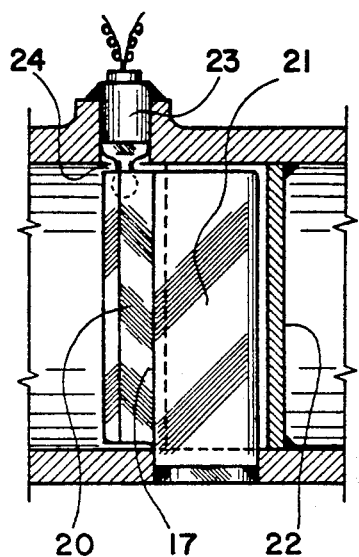
FIG. 4 illustrates another cross section of the embodiment shown in FIG. 3, that illustrates the vortex generator-sensor disposed across the cross section of the flow passage of variable cross section area.

In FIG. 4 there is illustrated an elevation view of the vortex generator-sensor 17, that is taken across plane 4—4 as shown in FIG. 4. The transducer 23 is connected to one extremity of the bluff body by a coupling or joint 24 providing a degree of flexibility. It should be understood that the combination of the vortex generator-sensor comprising separate bluff body 15 and planar sensor 16 shown in FIG. 3 may be replaced by another vortex generator-sensor of an integrated construction similar to the element 17, or the vortex generator-sensor 17 may be replaced by the combination of separate vortex generator 15 and sensor 16. The embodiment of the mass-volume vortex flowmeter shown in FIGS. 3 and 4 operates on the same principles as described by equations (1) and (4).

Figure 5:
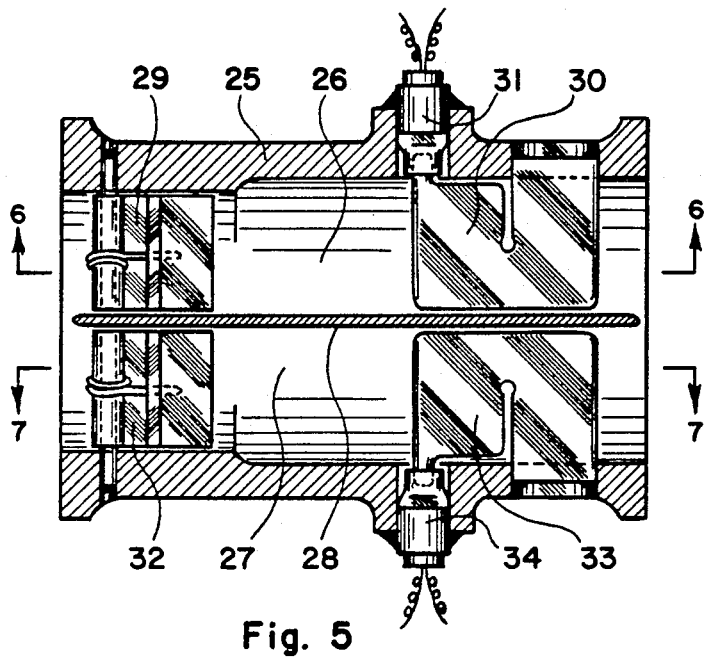
FIG. 5 illustrates a further embodiment of the mass-volume vortex meter comprising two parallel flow passages respectively including a fixed width vortex generating bluff body and a variable width vortex generating bluff body.

In FIG. 5 there is illustrated a cross section of a further embodiment of the mass-volume vortex shedding flowmeter. The flowmeter body 25 has two flow passages 26 and 27 separated from one another by a divider plate 28. The first flow passage 26 has a vortex generating bluff body 29 of fixed width and a vortex sensor including a planar member 30 connected to a transducer 31, while the second flow passage 27 has a vortex generating bluff body 32 of variable width and a vortex sensor including a planar member 33 connected to a transducer 34.

Figure 6:
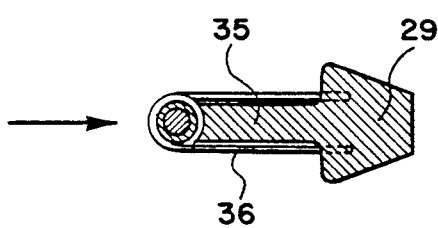
FIG. 6 illustrates a cross section of the fixed width vortex generating bluff body included in the embodiment shown in FIG. 5.

In FIG. 6 there is illustrated a cross section of the vortex generating bluff body 29 taken along plane 6—6 as shown in FIG. 5. The bluff body 29 includes a planar leading edge extension 35 and a dummy spring 36 in order to match the flow resistance characteristics of the bluff body 32 at fully folded position.

Figure 7:
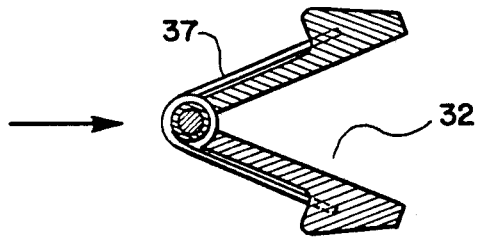
FIG. 7 illustrates a cross section of the variable width vortex generating bluff body included in the embodiment shown in FIG. 5.

In FIG. 7 there is illustrated a cross section of the vortex generating bluff body 32 taken along plane 7—7 as shown in FIG. 5. The bluff body 32 of variable width has essentially the same construction as that of the element 6 described in conjunction with FIG. 2 with one exception being that the spring 37 providing the bias force is now disposed at the upstream edge of the bluff body 32.

Figure 8:
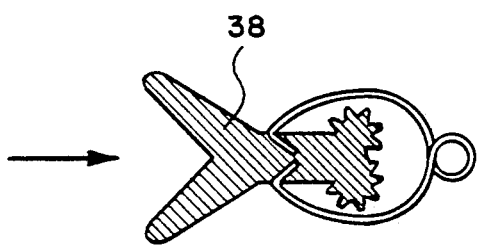
FIG. 8 illustrates a cross section of another fixed width vortex generating bluff body usable in place of that shown in FIG. 6.
Figure 9:
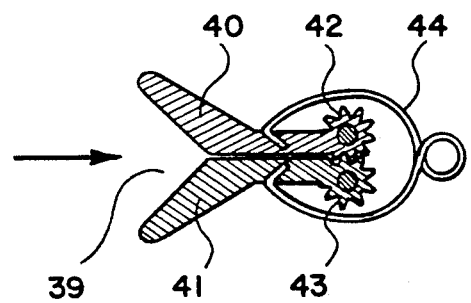
FIG. 9 illustrates a cross section of another variable width vortex generating bluff body usable in place of that shown in FIG. 7.

In FIG. 8 there is illustrated a cross section of another embodiment of the vortex generating bluff body 38 of fixed width that has a cross section matched to the counter-part thereof with variable width shown in FIG. 9.

In FIG. 9 there is illustrated a cross section of another embodiment of the vortex generating bluff body 39 of variable width, which includes the two halves 40 and 41 respectively pivoting about two pivot axis 42 and 43 in a gear-coupled movement and a spring 44 providing a bias force that tends to keep the width of the bluff body at the minimum value. The dynamic pressure of the fluid flow increases the bluff body width by spreading the two halves thereof, which contrasts the bluff body of variable width 6 shown in FIGS. 1 and 2 and the element 32 shown in FIGS. 5 and 7, wherein the dynamic pressure of the fluid flow decreases the bluff body width. It should be mentioned that the pivoting movements of the two halves of the bluff body of variable width shown in FIG. 2 or 7 may be coupled to one another by the meshing of the gear teeth as shown in FIG. 9. It should be understood that the pair of the bluff bodies employed in the embodiments shown in FIG. 2 or FIGS. 8 and 9 may be employed in place of the pairs 29 and 32 shown in FIGS. 6 and 7 in constructing the mass-volume flowmeter shown in FIG. 5.

While the principles of the present invention have now been made clear by the illustrative embodiments, there will be many modifications of the structures, arrangements, proportions, elements and materials obvious to those skilled in the art, which are particularly adapted to the working environments and operating conditions in the practice of the invention without departing from those principles. It is not desired to limit the inventions to the particular illustrative embodiments shown and described and, accordingly, all suitable modifications and equivalents may be regarded as falling within the scope of the inventions as defined by the claims which follow.

The embodiments of the invention, in which an exclusive property or priviledge is claimed are defined as follows:

1. An apparatus for measuring flow of fluid comprising in combination:
    (a) a body including a flow passage;
    (b) a first vortex generator of elongated shape with fixed width disposed across a first cross section of the flow passage, and means for measuring frequency of vortex shedding from the first vortex generator;
    (c) a second vortex generator of elongated shape with a variable width disposed across a second cross section of the flow passage wherein said variable width of the second vortex generator varies as a function of flow rate of fluid moving through the flow passage, and means for measuring frequency of vortex shedding from the second vortex generator;
    (d) means for determining volume flow rate of the fluid from the frequency of vortex shedding from the first vortex generator; and
    (e) means for determining mass flow rate of the fluid from a combination of the frequency of vortex shedding from the first vortex generator and a function of the frequency of vortex shedding from the first vortex generator and the frequency of vortex shedding from the second vortex generator.

2. The combination as set forth in claim 1 wherein density of the fluid is determined from ratio of the mass flow rate to the volume flow rate.

3. An apparatus for measuring flow of fluid comprising in combination:
    (a) a body including a flow passage;
    (b) a first vortex generator of elongated shape with fixed width disposed across a first cross section of the flow passage with fixed cross section area, and means for measuring frequency of vortex shedding from the first vortex generator;
    (c) a second vortex generator of elongated shape with fixed width disposed across a second cross section of the flow passage with variable cross section area varying as a function of flow rate of fluid moving through the flow passage, and means for measuring frequency of vortex shedding from the second vortex generator;
    (d) means for determining volume flow rate of the fluid from the frequency of vortex shedding from the first vortex generator; and
    (e) means for determining mass flow rate of the fluid from a combination of the frequency of vortex shedding from the first vortex generator and a function of the frequency of vortex shedding from the first vortex generator and the frequency of vortex shedding from the second vortex generator.

4. The combination as set forth in claim 3 wherein density of the fluid is determined from ratio of the mass flow rate to the volume flow rate.

5. An apparatus for measuring flow of fluid comprising in combination:
    (a) a body including a first and second flow passages disposed in a parallel arrangement;
    (b) a first vortex generator of elongated shape with fixed width disposed across a cross section of the first flow passage, and means for measuring frequency of vortex shedding from the first vortex generator;
    (c) a second vortex generator of elongate shape with variable width disposed across a cross section of the second flow passage wherein said variable width of the second vortex generator varies as a function of flow rate of fluid moving through the apparatus, and means for measuring frequency of vortex shedding from the second vortex generator;
    (d) means for determining volume flow rate of the fluid from an additive combination of the frequency of vortex shedding from the first vortex generator and the frequency of vortex shedding from the second vortex generator; and (e) means for determining mass flow rate of the fluid from a combination of the volume flow rate of the fluid and a function of the frequency of vortex shedding from the first vortex generator and the frequency of vortex shedding from the second vortex generator.

6. The combination as set forth in claim 5 wherein density of the fluid is determined from the ratio of the mass flow rate to the volume flow rate.

* * * * *